United States Patent
Axelsson et al.

(10) Patent No.: US 9,820,559 B2
(45) Date of Patent: Nov. 21, 2017

(54) CLEANING DEVICE USED FOR CLEANING AN IMPLANT OR FOR THE DEBRIDEMENT OF AN IMPLANT SURFACE

(75) Inventors: Robert Axelsson, Granna (SE); Lars Magnus Bjursten, Limhamn (SE); Niklas Johansson, Jonkoping (SE); Erik Lennings, Huskvarna (SE); Janarne Wetterheim, Jonkoping (SE); Christer Nilsson, Ostersund (SE); Ove Sundelin, Froson (SE); Rickard Olsson, Brunflo (SE)

(73) Assignee: Tigran Technologies AB (PUBL), Malmo (SE)

( * ) Notice: Subject to any disclaimer, the term of this patent is extended or adjusted under 35 U.S.C. 154(b) by 547 days.

(21) Appl. No.: 13/701,363

(22) PCT Filed: Jun. 1, 2011

(86) PCT No.: PCT/SE2011/050684
§ 371 (c)(1),
(2), (4) Date: Feb. 11, 2013

(87) PCT Pub. No.: WO2011/152789
PCT Pub. Date: Dec. 8, 2011

(65) Prior Publication Data
US 2013/0139850 A1    Jun. 6, 2013

Related U.S. Application Data

(60) Provisional application No. 61/344,172, filed on Jun. 3, 2010.

(30) Foreign Application Priority Data

Jun. 3, 2010   (SE) ..................................... 1050570

(51) Int. Cl.
*A61F 2/30*     (2006.01)
*A61B 1/12*     (2006.01)
(Continued)

(52) U.S. Cl.
CPC ................ *A46B 3/00* (2013.01); *A46B 9/005* (2013.01); *A61C 8/0089* (2013.01);
(Continued)

(58) Field of Classification Search
CPC .. A61C 3/005; A61C 8/0089; A46B 2200/108
See application file for complete search history.

(56) References Cited

U.S. PATENT DOCUMENTS 2,637,061 A  *  5/1953  Ozdobinski ..................... 15/226
5,067,195 A  *  11/1991 Sussman ....................... 15/167.1
(Continued)

FOREIGN PATENT DOCUMENTS

CH    EP 1679017 A1 *   7/2006    ............. A46B 3/005
DE       3510377           9/1986
(Continued)

OTHER PUBLICATIONS

English Machine Translation of DE 4019830 A1.*
(Continued)

*Primary Examiner* — Nicole Blan
(74) *Attorney, Agent, or Firm* — Meyertons, Hood, Kivlin, Kowert & Goetzel, P.C.; Mark R. DeLuca

(57) ABSTRACT

The present invention describes a cleaning device used for cleaning an implant or for the debridement of an implant surface 1 comprising two combined main parts 2, 3, the first main part 2 being a handle shaft 2 which is stiff, plastic deformable or elastic deformable, the second main part 3 being at least one cleaning element 4 comprising a base part 5 and several bristles 6, bristle loops 7 or a cam 8 of spikes (Continued)

9, wherein the base part 5 is joined together with the handle shaft 2 so as to form a cleaning device 1 with a handle.

13 Claims, 4 Drawing Sheets

(51) Int. Cl.
    *A61C 8/00*     (2006.01)
    *A46B 3/00*     (2006.01)
    *A46B 9/00*     (2006.01)

(52) U.S. Cl.
    CPC .......... *A61F 2/30721* (2013.01); *A61B 1/122* (2013.01); *A61F 2002/30719* (2013.01)

(56) References Cited

U.S. PATENT DOCUMENTS

| | | | |
|---|---|---|---|
| 5,123,841 A * | 6/1992 | Millner | A61C 15/00 132/322 |
| 5,560,069 A | 10/1996 | Berger et al. | |
| 5,775,346 A | 7/1998 | Szyszkowski | |
| 5,802,667 A * | 9/1998 | Williams | A46B 13/02 134/21 |
| 5,940,923 A | 8/1999 | Gunning | |
| 6,325,626 B1 * | 12/2001 | Blass | 433/141 |
| 6,601,588 B1 * | 8/2003 | Baltierra et al. | 132/76.5 |
| 7,137,757 B1 * | 11/2006 | Cosban | A46B 3/18 138/97 |
| 2001/0016962 A1 * | 8/2001 | Moore et al. | 15/104.16 |
| 2003/0099916 A1 * | 5/2003 | McLean et al. | 433/102 |
| 2003/0224320 A1 | 12/2003 | Kandelman et al. | |
| 2004/0122447 A1 | 6/2004 | Harmon et al. | |
| 2004/0255414 A1 * | 12/2004 | Tulipana | B08B 1/04 15/104.04 |
| 2006/0074425 A1 * | 4/2006 | Sutterlin et al. | 606/79 |
| 2006/0195994 A1 * | 9/2006 | Hung | B65H 75/364 15/104.095 |
| 2007/0288042 A1 * | 12/2007 | Serbousek et al. | 606/160 |
| 2008/0318184 A1 * | 12/2008 | Zargari et al. | 433/119 |
| 2010/0015567 A1 * | 1/2010 | Elbaz et al. | 433/89 |

FOREIGN PATENT DOCUMENTS

| | | | |
|---|---|---|---|
| EP | 1779808 | 5/2007 | |
| JP | H3-123588 | 12/1991 | |
| JP | H3-123588 U | * 12/1991 | |
| JP | DE 4019830 A1 * | 1/1992 | ............ A46B 3/18 |
| JP | 2003245287 | 9/2003 | |
| JP | 2006-340749 | 12/2006 | |
| WO | 2004/024005 | 3/2004 | |
| WO | 2007055195 | 5/2007 | |
| WO | 2009/083281 | 7/2009 | |

OTHER PUBLICATIONS

EnglishTranslation of JP H3-123588 U.*
Merriam-Webster Definition of Bristle; p. 1.*
English Machine Translation of EP 1679017.*
Bristle_Definition of Bristle by Merriam Webster.*
Office Action for Chinese Patent Application No. 201180025646.X dated Aug. 1, 2014.
International Search Report for PCT Application No. PCT/SE2011/050684 dated Sep. 22, 2011.
Written Opinion for PCT Application No. PCT/SE2011/050684 dated Sep. 22, 2011.
International Preliminary Report on Patentability for PCT Application No. PCT/SE2011/050684 dated Dec. 4, 2012.
Office Action for Japanese Patent Application No. 2013-513140 dated May 22, 2015.
Notice of Allowance for Japanese Patent Application No. 2013-513140 dated Jan. 12, 2017 with allowed claims and Office Action issued prior to allowance (dated May 22, 2015, previously cited).

* cited by examiner

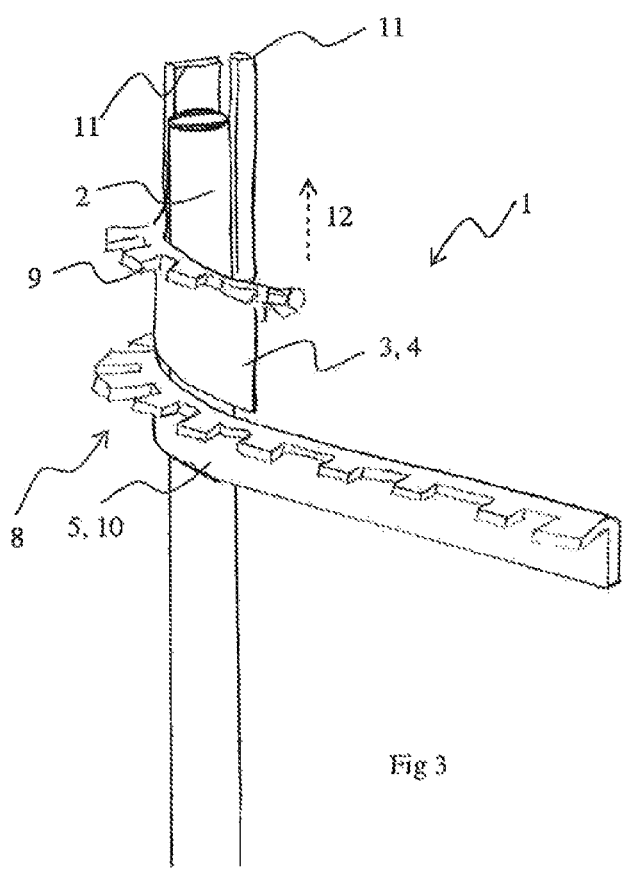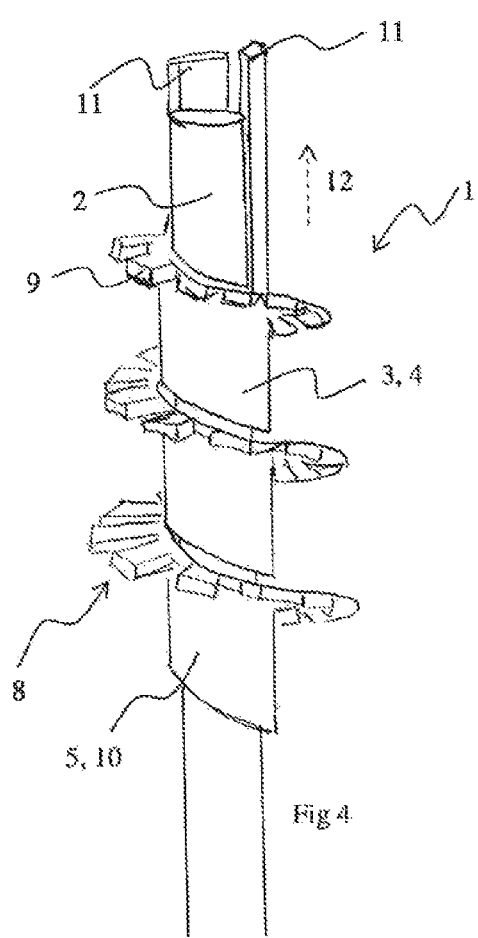

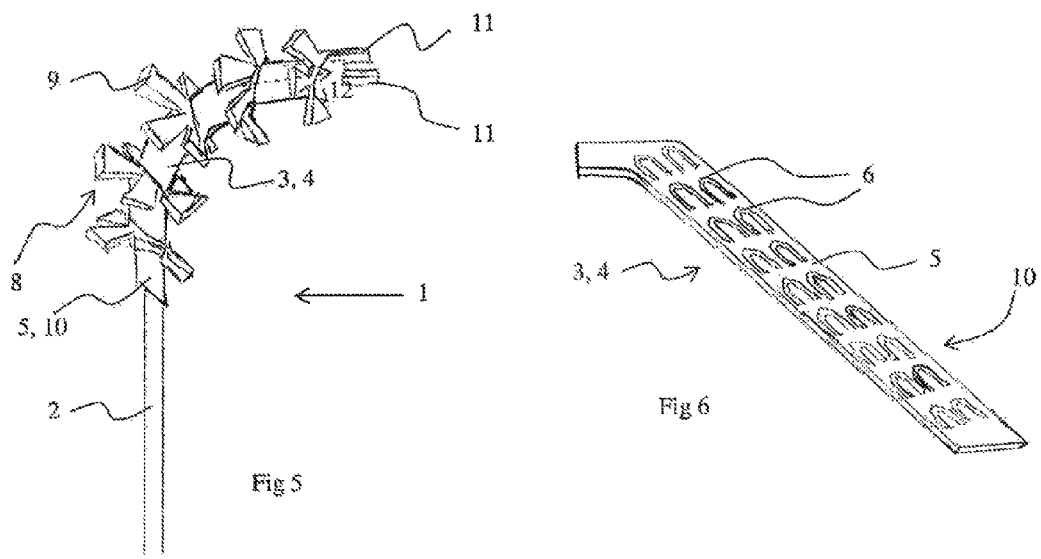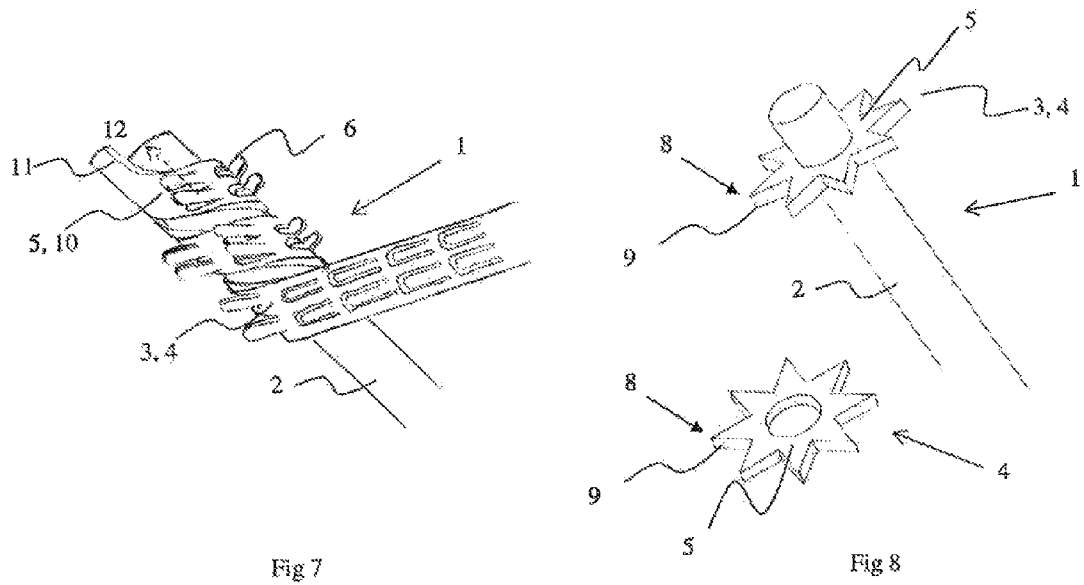

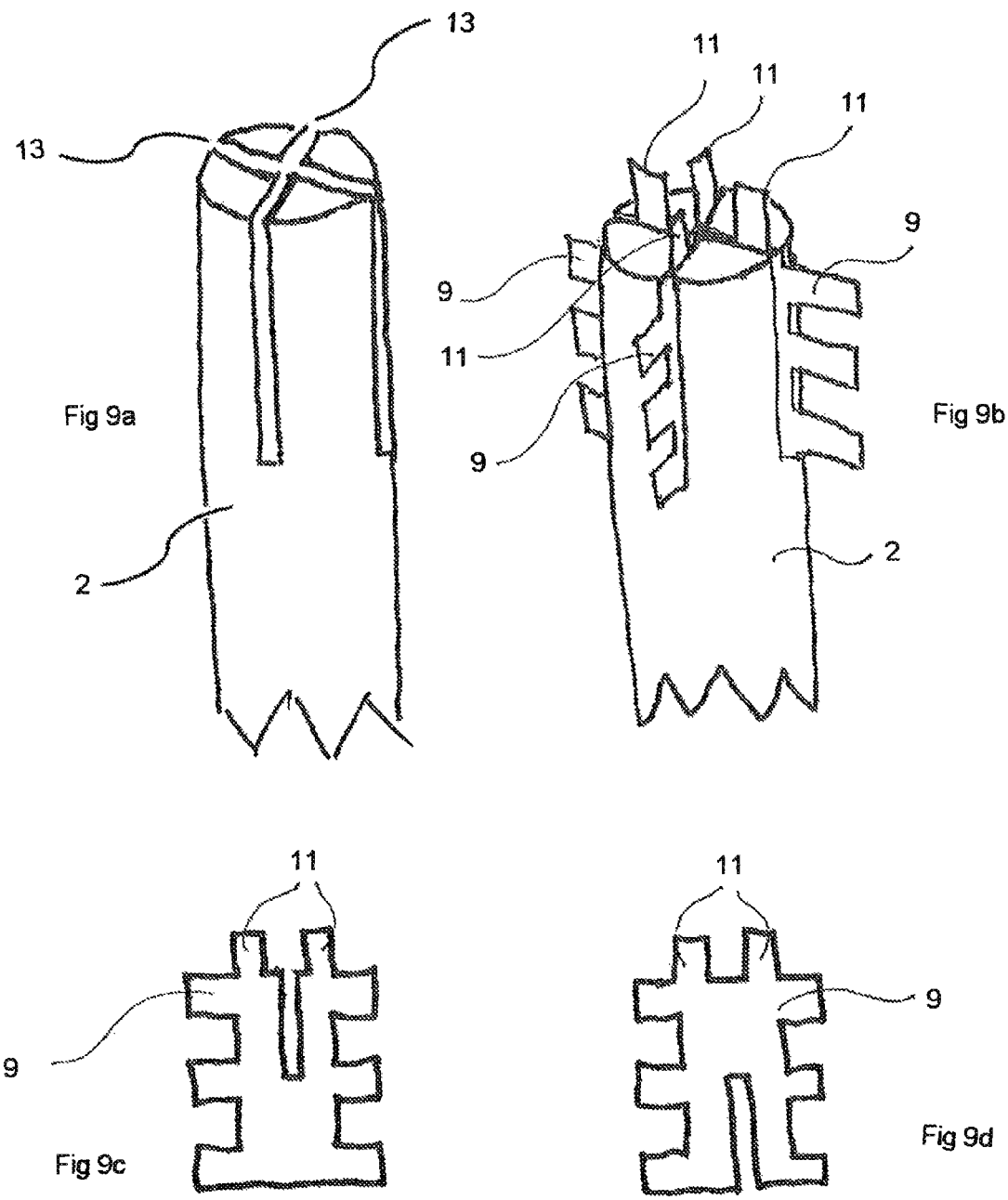

CLEANING DEVICE USED FOR CLEANING AN IMPLANT OR FOR THE DEBRIDEMENT OF AN IMPLANT SURFACE

FIELD OF INVENTION

The present invention relates to a cleaning device, particular a cleaning device intended for medical applications, such as e.g. for cleaning an implant or for the debridement of an implant surface.

TECHNICAL BACKGROUND

Different forms of cleaning devices, such as brushes, have been long known. One such type is the brushes configured as the so called twisted-in-wire brushes. For example in WO 2009/083281 there is described a medical cleaning tool comprising an elongated base member formed of at least two wires being twisted with each other, i.e. the tool has a twisted-in-wire configuration. Moreover, the cleaning tool comprises a plurality of titanium or titanium alloy bristles fixed between the twisted wires and extending away from the twisted wires.

There are several drawbacks with the brush described in WO 2009/083281. The first is related to the manufacturing process. When producing a twisted-in-wire brush, the bristles have to be applied sequential, i.e. one bristle after another. This drawback is in fact also valid for other types of known brushes. Moreover, in view of the specific twisted-in-wire configuration, the stem needs to meet stringent mechanical requirements to retain the bristles and this makes the stem very inflexible.

Furthermore, in U.S. Pat. No. 2,637,061A there is disclosed a brush construction comprising an elongated handle, a strip of flexible sheet material having a folded portion and a tail portion, said folded portion being slit throughout the fold to provide loop bristles throughout a part of its width and providing for an unslit part, said folded portion being wound upon the end of the handle by its unslit part and the tail portion being wound with over-lapping turns along the length of the handle.

One object of the present invention is to provide a cleaning device, which is easy and as such inexpensive to produce. Another object of the present invention is to provide a cleaning device concept having high customer flexibility, i.e. which is possible to use for producing cleaning devices with different properties depending on the customer needs. One such property not possible to obtain with the traditional twisted in wire configuration is a flexible shaft that returns to the straight position once it is released after being bent.

SUMMARY OF INVENTION

The objects of the present invention are solved by a cleaning device comprising two combined main parts,
the first main part being a handle shaft which is stiff, plastic deformable or elastic deformable;
the second main part being at least one cleaning element comprising a base part and several bristles, bristle loops or a cam of spikes;
wherein
the base part is joined together with the handle shaft so as to form a cleaning device with a handle.

It should be noted that the cleaning device disclosed in U.S. Pat. No. 2,637,061A does not comprise several bristles, bristle loops or a cam of spikes. Although the expression "loop bristles" is used in U.S. Pat. No. 2,637,061A, it is clear from the figures in U.S. Pat. No. 2,637,061A that it is a grooved strip being wound around the handle. Furthermore, both the materials used for the brush in U.S. Pat. No. 2,637,061A as well as the intended use of the brush according to U.S. Pat. No. 2,637,061A differ very much from the materials and the intended use of the cleaning device according to the present invention.

As may be noted above, the cleaning device according to the present invention comprises two main parts. This fact and also how these two main parts are joined together render many advantages. Firstly, it is according to the present invention possible to produce a cleaning device having a handle which is stiff, plastic deformable or elastic deformable. This is not possible for e.g. a twisted-in-wire brush with its twisted configuration. A twisted-in-wire brush may only be produced to be stiff or plastic deformable. Moreover, when a twisted-in-wire brush is bent, if being plastic deformable, it may not achieve a symmetrical rotation axis. That is, it may not be rotated symmetrically after being bent. However, with the cleaning device according to the present invention, the material of the handle can be chosen freely to achieve the desired properties of the handle, i.e. the configuration is not limited in any way. Secondly, when producing the cleaning device according to the present invention, no such limiting factor such as the provision of bristles one by one is needed. The second main part should instead only be joined together with the handle and the cleaning device is thereby produced. As an example, according to the present invention, it is possible to produce a cleaning device which is both elastic deformable and which also has a symmetrical rotation axis while being bent.

Furthermore, according to one specific embodiment of the present invention, the base part is joined together with the handle shaft and around the handle shaft so as to form a cleaning device with a handle around.

According to yet another embodiment of the present invention, the second main part is (at least) two separate cleaning elements each comprising a base part and several spikes and wherein each base part is joined together with the handle shaft by being inserted in a continuous groove in the handle shaft. These embodiments are further described below.

BRIEF DESCRIPTION OF THE DRAWINGS

FIG. 3 shows the winding of the cleaning element according to FIGS. 1 and 2 around a handle shaft to form a cleaning device according to the present invention.

In FIG. 4 the winding is completed and a cleaning device according to the present invention is produced.

Also FIG. 5 shows the same cleaning device as in FIG. 4, however in this case the cleaning device has been bent, such as before use or during use.

FIG. 6 shows another cleaning element according to the present invention. In this case the cleaning element comprises a base part and several bristles, but also a form of an end spike.

FIG. 7 shows the winding of a cleaning element according to FIG. 6 around a handle shaft to form a cleaning device according to the present invention.

FIG. 8 shows another specific embodiment of the present invention. In this case the cleaning device comprises a handle shaft and several cleaning elements, in this case in the shape of "throwing stars", which are joined together with the handle shaft and around the handle shaft. In FIG. 8 one of the "throwing stars" is already been joined together with the handle shaft and another one, also depicted, is just about to be joined together with the handle shaft.

FIG. 9a-9d show another specific embodiment according to the present invention, where the second main part is two separate cleaning elements each comprising a base part and several spikes and where the two base parts are joined together with the handle shaft by being inserted in a continuous groove in the handle shaft.

SPECIFIC EMBODIMENTS OF THE INVENTION

Figure 1:
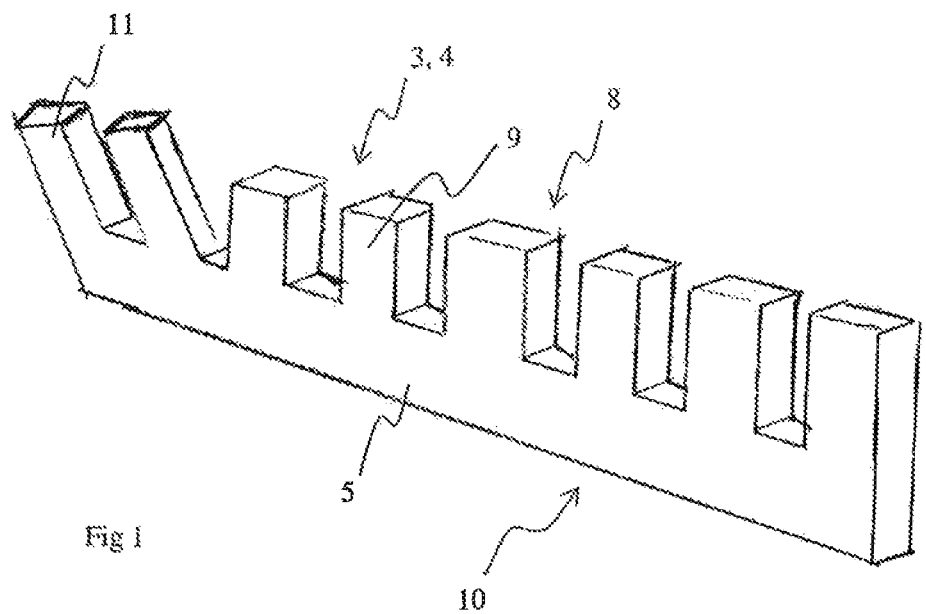
FIG. 1 shows a second main part, namely a cleaning element of a cleaning device according to the present invention. In this case the cleaning element comprises a base part and a cam of spikes.

One advantage with the cleaning device according to the present invention is the possibility to use different types of handle shafts. According to one specific embodiment of the present invention, the handle shaft is stiff. Possible materials for such a handle shaft are e.g. wood, metal or rigid polymers. With "stiff" herein is meant "non-deformable". According to another specific embodiment of the present invention, the handle shaft is plastic deformable. According to this embodiment, the handle shaft is possible to bend to a new shape without being flexed back to its original shape. According to yet another specific embodiment of the present invention, the handle shaft is elastic deformable, i.e. the handle shaft is possible to bend but it flexes back to its original shape afterwards. This may according to the present be advantageous for some specific applications, such as when used for e.g. cleaning implant surfaces which are difficult to get into contact with. One material which is suitable to use when the handle shaft should be elastic deformable is nitinol, which is a nickel/titanium alloy.

Also, the second main part of the cleaning device may comprise different materials. According to one specific embodiment of the present invention, the base part is made of a metal, metal alloy or a polymeric material. According to another embodiment, the base part is made of titanium or an alloy thereof, tantalum or an alloy thereof, niobium or an alloy thereof, or zirconium or an alloy thereof. These materials are particularly suitable for cleaning devices intended for cleaning or debriding an implant surface. As many implants may comprise these materials, especially dental implants, it may be preferred to have a cleaning device with a second main part with e.g. bristles or a cam of spikes according to the present invention also being made of these materials. When such a cleaning device according to the invention is used for cleaning or debridement of an implant surface, there is minimal risk of contamination of the implant from the cleaning device comprising the same material as the implant.

According to one specific embodiment of the present invention, the bristles, bristle loops or cam of spikes are made of a metal, metal alloy or a polymeric material. As may be understood from above, according to one embodiment, the bristles, bristle loops or cam of spikes are made of titanium or an alloy thereof, tantalum or an alloy thereof, niobium or an alloy thereof, or zirconium or an alloy thereof. As is evident from above, the entire second main part may be made of one and the same material, such as e.g. titanium or a titanium alloy. Therefore, according to one embodiment of the invention, the cleaning element with its base part and several bristles, bristle loops or a cam of spikes is made in one piece.

It is important to understand that the bristles, bristle loops or cam of spikes may have any shapes according to the present invention. For example, the expression "bristles" should be interpreted to imply any shape like tips, spikes, points or the like. The common feature for the bristles, bristle loops or cam of spikes in relation to the present invention are that they protrude out from the handle shaft of the cleaning device when the cleaning element have been joined together with the handle shaft. The expression "bristles" should thus not be confused to only imply typical shaped bristles on a standard brush. Moreover, as mentioned above, bristles of known brushes have been applied one by one, which is not the case in relation to the bristles, spikes, tips etc. according to the present invention. Moreover, the expression "bristle loops" refers to single bristles extending from the second main part or the at least one cleaning element but where these bristles are joined together to form a loop extending from said cleaning element. In other words, each bristle loop is joined together with the cleaning device at two places, and not only at one place such as in the case of a single bristle. Furthermore, as disclosed below, the bristles or bristles loops according to the present invention may also be seen as cutting elements as they are possible to provide so that they are flexible or resilient in one rotation direction of the cleaning device but stiff and cutting in the other rotation direction.

Moreover, it is important to understand that the cleaning device according to the present invention also may comprise several cleaning elements. One such example is a cleaning device having several cleaning elements e.g. in the form of rings with projecting tops ("throwing stars", see FIG. 8) being fixed around the handle shaft at different positions along the handle shaft. Another example is a cleaning device according to the invention having e.g.

two cleaning elements forming a double helix around the handle shaft when the cleaning elements are coiled around the handle shaft. Nevertheless, in all possible embodiments according to the present invention, at least one cleaning element comprising a base part and several bristles, bristle loops or a cam of spikes is joined together via the base part with the handle shaft so as to form the cleaning device.

As is evident from above, the cleaning element may be in different shapes. According to one specific embodiment of the present invention, the cleaning element is in the form of a strip, which is wound around the handle shaft to be joined together with the same. Bringing the strip together with the handle shaft may be performed in different ways. One example is by adhesion using some form of adhesive substance, such as different glues. Another example is by welding or fusing. Moreover, the handle shaft may be provided with slits, grooves, hacks or indents so that a strip may be fastened or pinched to the handle shaft by use of the slits, grooves, hacks or indents. If the cleaning elements are in the form of e.g. "throwing stars" rings, the handle shaft may also be provided with e.g. slits, grooves, hacks, indents or protruding portions which are flexible in only one direction, so that the rings may med fixated along the handle shaft.

According to one specific embodiment of the present invention, when the cleaning element is in the form of a strip, the cleaning element comprises a cam of spikes, each spike extending from the base part. This is shown in the figures. According to one specific embodiment, the length of the spikes is different. This embodies all kind of different configurations of the cam of spikes to give the cleaning device different diameters along the shaft, such as a concave shape, convex shape or a totally irregular shape where longer spikes are followed by shorter spikes which again are followed by longer spikes, etc.

According to yet another embodiment of the present invention, the length of the spikes decreases from one end of the base part towards the other end of the base part. According to another specific embodiment, the length of the spikes increases from one end of the base part towards the other end up to a point along the base part and thereafter decreases. Furthermore, according to one specific embodiment of the present invention, at least one end spike is provided to extend essentially in the same direction as the length axis of the handle shaft. This is shown in the figures. As may be seen, the end spike or end spikes have an angled direction in comparison to the other spikes of the cam. Moreover, as shown in the figures, they may be longer than the other spikes. These end spikes are directed so that when the strip is coiled around the handle shaft, the end spikes will extend essentially in the same direction as the length axis of the handle shaft. One may say that they form a starting point for the coiling or winding of the strip around the handle shaft during the production of the cleaning device.

According to another embodiment of the present invention, there are provided bristles or bristle loops on the cleaning element. Also in this case one could say that the cleaning element is in the form of a strip, however, in this case there is no cam of spikes protruding in the same plane as the cam. According to this embodiment, the bristles or bristle loops protrude from the surface of the strip. The bristle or bristle loops may be protruding from the surface of the cleaning element before the cleaning element is joined together with the handle shaft. However, according to one embodiment of the present invention, the bristles or bristle loops are folded out, extending from the cleaning element when the cleaning element is wound around the handle shaft to be joined together with the same. According to this embodiment, the bristle or bristle loops are lying on the surface of the cleaning element before the joining, but will fold out when the coiling or winding is made. According to one specific embodiment, the strip forming the cleaning element has an extended portion on one end. This extended portion also forms a starting point for the winding around the handle shaft of such a form of strip or cleaning element according to the invention. Such an extended portion is also shown in the figures. In this context it is important to understand that the parts forming the bristles may protrude from either the edge and/or the surface of the cleaning element according to the present invention.

According to one specific embodiment of the present invention, the handle shaft is hollow. Such a hollow handle shaft is intended to create a possibility to add a fluid to the site of cleaning or debridement. According to one embodiment, the handle shaft is hollow at both ends. According to another embodiment, the handle shaft is only hollow from the fluid feeding end along the handle shaft, but not hollow at the other end of the handle shaft. However, according to this embodiment, the handle shaft has several perforations along the handle shaft allowing the fluid to be added to the site of cleaning or debridement from the hollow handle shaft. Different fluids may be possible to add, such as flushing fluids, medical cleaning fluids, sterilization fluids, and medicaments, etc. Specific examples are water, sterilized brine solutions, hydrogen peroxide solution, antibiotics, weak acid solutions or diluted hydrogen fluoride solution.

Moreover, the cleaning device according to the present invention may be adapted so that it can be connected to a rotation device. For example, the handle may have some kind of connection means which is intended to be connected into a motor-driven rotation unit, such as a contra-angle hand-piece. The cleaning device according to the present invention may thus be used manually or together with a rotation unit, e.g. via an adapter or a connection means.

The cleaning device components, i.e. the first and second main part, may be produced with known technologies, such as by casting, etching or e.g. injection moulding or extrusion for plastic materials. Moreover, wire drawing is also possible, such as in the case of nitinol wire. The cleaning device according to the present invention finds many different uses. Cleaning devices according to the present invention may be used for different industrial applications, however the main focus is for medical purposes. The cleaning device according to the present invention may e.g. be used for cleaning of surfaces and holes in the dentistry. One specific intended use is for the cleaning of an implant surface or for the debridement of an implant surface, particularly for dental implants. Therefore, according to one specific embodiment, there is disclosed the use of the cleaning device for cleaning or debridement of surfaces and holes in the dentistry. Furthermore, according to yet another embodiment, the intended use is for cleaning or debridement of an implant surface, such as a metallic implant surface, e.g. a metallic dental implant surface.

According to another specific embodiment, the intended use is for industrial cleaning. When used in this application the possibility to have a rotating cleaning device that can be inserted into a curved pipe or into a cavity or orifice that is not accessible with a brush with a stiff shaft. The fact that the cleaning device always flexes back to its original shape has advantages in specific situations.

DETAILED DESCRIPTION OF THE DRAWINGS

FIG. 1 shows a second main part 3 being a cleaning element 4 according to the present invention. The cleaning element 4 comprises a base part 5 and a cam 8 of spikes 9. Two end spikes 11 are provided on one end of the cleaning element 4. Moreover, the cleaning element 4 is in the form of a strip 10 which is intended to be wound around a handle shaft 2 to be joined together with the handle shaft 2.

Figure 2:
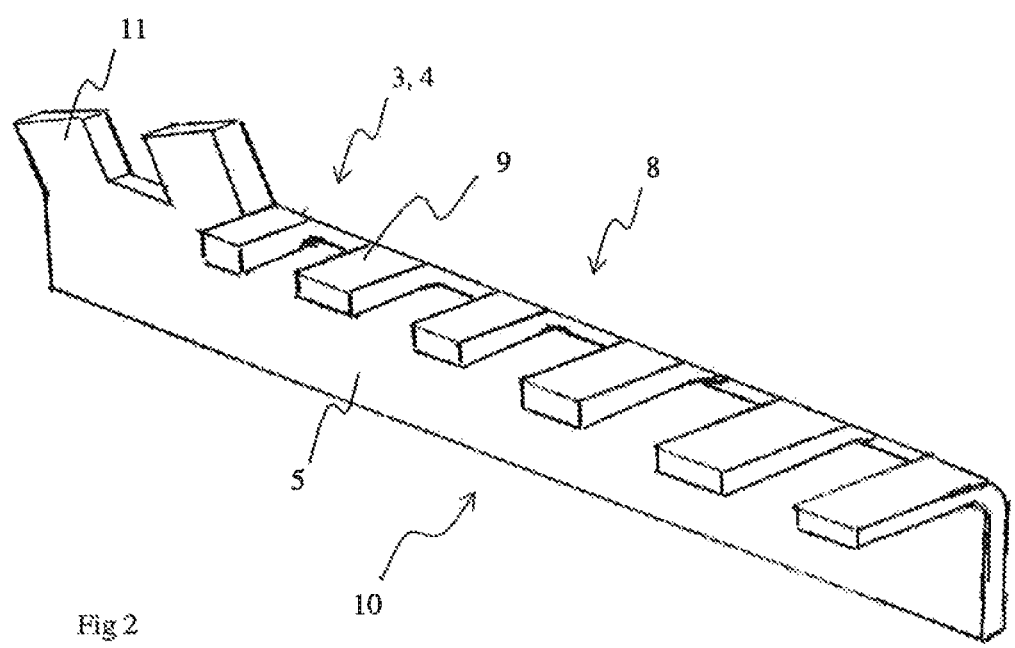
FIG. 2 shows the same cleaning element as in FIG. 1, however in this case the cam of spikes, except the two end spikes, have been bent before being wound around a handle shaft to form a cleaning device according to the present invention.

FIG. 2 shows the same cleaning element 4 as in FIG. 1, however in this case the cam 8 of spikes 9, except the two end spikes 11, have been bent.

FIG. 3 shows the winding of the cleaning element 4 in FIG. 2, where the cam 8 of spikes 9 has been bent around a handle shaft 2 to form a cleaning device 1 according to the present invention. The end spikes 11 are provided so that they extend essentially in the same direction as the length axis 12 of the handle shaft 2. In FIG. 4, the winding is completed and a cleaning device 1 according to the present invention has been produced.

Also FIG. 5 shows the same cleaning device 1 as in FIG. 4, however in this case the cleaning device 1 has been bent, such as before use or during use. This implies that the handle shaft 2 in this case is either plastic deformable and e.g. made of titanium or an alloy thereof, tantalum or an alloy thereof, niobium or an alloy thereof, or zirconium or an alloy thereof, or elastic deformable and e.g. made of nitinol.

FIG. 6 shows another cleaning element 4 according to the present invention. In this case the cleaning element 4 comprises a base part 5 and several bristles 6. The cleaning element 4 forming a strip 10 which is intended to be wound around a handle shaft 2 also comprises an end spike 11. It is important to realize that the bristles 6 could be joined bristle loops 7 instead, and that such a cleaning element 4 having several bristle loops 7 also is part of the scope of the present invention. Moreover, the bristles 6 may have any shape according to the present invention.

FIG. 7 shows the winding of a cleaning element 4 according to FIG. 6 around a handle shaft 2 to form a cleaning device 1 according to the present invention. As may be seen, the end spike 11 is provided so that is extends essentially in the same direction as the length axis 12 of the handle shaft 2. Moreover, in this case, during the winding of the cleaning element 4 around the handle shaft 2, the bristles 6 are prone to bent outwards so that the bristles 6 extend out from the handle shaft 2. As may be understood from FIG. 7, the bristles 6 may be provided to be flexible or resilient in one rotation direction but stiff and cutting in the other rotation direction of the handle shaft 2.

FIG. 8 shows another specific embodiment of the present invention. In this case the cleaning device 1 comprises a handle shaft 2 and several cleaning elements 4, in this case in the shape of "throwing stars". The cleaning elements 4 are joined together with the handle shaft 2 and around the handle shaft 2. Each cleaning element 4 has a base part 5. Moreover, in this case, each cleaning element 4 also has a cam 8 of spikes 9. Other shapes are of course also possible. In FIG. 8 one of the "throwing stars" is already been joined together with the handle shaft 2 and another one, also depicted, is just about to be joined together with the handle shaft 2. It is important to realize that also other cleaning devices 1 having several cleaning elements 4 are possible according to the present invention. One example is a double helix where two strips 10 like the one showed in FIGS. 1 and 2 are wound around the handle shaft 2.

FIG. 9a-9d show another specific embodiment according to the present invention. In FIG. 9a there is shown a handle shaft 2 having grooves 13. FIG. 9b shows a cleaning device 1 according to the present invention, where the second main part 3, which is two separate cleaning elements 4 shown in FIG. 9c and FIG. 9d, respectively, and each comprising a base part 5 and several spikes 9, has been joined together with the handle shaft 2 by each separate cleaning elements 4 being inserted in a continuous groove 13 in the handle shaft 2. By using a handle shaft 2 that is cut open into 2 or 4 parts or prongs (continuous grooves 13) (see FIG. 9a), one or two sheets (see FIG. 9c and FIG. 9d) of the material used for the cleaning action may be wedged in between the prongs and then secured using welding or by other methods of bonding like glues or adhesives. When such two cleaning elements 4 in the form of two sheets are used, they need to have slots (shown in FIG. 9c and FIG. 9d) in order to fit together in the grooves 13 of the handle shaft 2. The shape of the final cleaning device 1 is shown in FIG. 9b. Furthermore, the spikes 9 as well as the possible end spikes 11 are shown in FIG. 9b-9d.

The use of the cleaning device according to the invention is as indicated above not limited to dental use but may be used in several other applications, especially when there is a need to have a rotating brush attached to a flexible shaft. This specific embodiment shown in FIG. 9a-9d allows the cleaning device to be inserted into a curved pipe or into a cavity or orifice that is not accessible with a brush with a stiff shaft. The fact the cleaning device always flexes back to its original shape has advantages in specific situations.

CONCLUSIONS

The cleaning device according to the present invention has many advantages. Firstly, the handle may be stiff, plastic deformable or elastic deformable, which is not possible with other known brush production concepts, such as e.g. a twisted-in-wire brush. Secondly, the concept of having two different main parts being joined together as to form the cleaning device provides an easy and inexpensive production mode in comparison to the adhesion of bristles one by one. Moreover, this concept according to the present invention, enables e.g. a cleaning device which is symmetrically rotatable also in bent state during use to be produced. This is not possible with e.g. the twisted-in-wire production mode. Moreover, according to the present invention, the liberty of designing the second main part, which is the actual cleaning part, for specific purposes and applications is very large. As an example, according to the present invention it is possible to provide a cleaning device having a cleaning element comprising bristles or bristle loops which are flexible or resilient in one rotation direction but stiff and cutting in the other rotation direction.

Furthermore, in order to combine the advantageous properties of various materials and at the same time make the device possible to produce without elaborate procedures the cleaning device concept according to the present invention was developed. The device is especially targeted to use the beneficial properties of Nitinol® and titanium for cleaning in the dental area. The Nitinol® in the stem or handle shaft provides for flexibility also when the cleaning device is put in a rotating hand piece, the titanium is advantageous when the cleaning is performed close to a dental implant as then it provides good cleaning properties and at the same time will not leave any detrimental debris on the implant surface. Other materials than titanium may be used like polymers, where nylon has a long history of successful uses as brush bristles.

The invention claimed is:

1. A cleaning device for cleaning or debridement of surfaces and holes in teeth of a subject or for cleaning or debridement of an implant surface, comprising two combined main parts,
   the first main part being a handle shaft which is elastically deformable;
   the second main part being a cleaning element comprising a base part and several bristles, bristle loops or a cam of spikes coupled to the base part, wherein the bristles, bristle loops or cam of spikes are made of titanium or an alloy thereof, tantalum or an alloy thereof, niobium or an alloy thereof, or zirconium or an alloy thereof, wherein the cleaning element with its base part and several bristles, bristle loops or a cam of spikes is made from one piece, wherein the cleaning element is in the form of a strip which is wound around the handle shaft to be joined together with the same; and wherein
   the base part is joined together with the handle shaft so as to form a cleaning device with a handle; and wherein the cleaning device is adapted so that it can be connected to a rotation device.

2. The cleaning device according to claim 1, wherein the handle shaft is made of nitinol.

3. The cleaning device according to claim 1, wherein the cleaning element comprises a cam of spikes, each spike extending from the base part.

4. The cleaning device according to claim 3, wherein the length of the spikes is different.

5. The cleaning device according to claim 3, wherein the length of the spikes decreases from one end of the base part towards the other end of the base part.

6. The cleaning device according to claim 3, wherein the length of the spikes increases from one end of the base part towards the other end up to a point along the base part and thereafter decreases.

7. The cleaning device according to claim 1, wherein at least one end spike is provided to extend essentially in the same direction as the length axis of the handle shaft.

8. The cleaning device according to claim 1, wherein there are provided bristles or bristle loops on the cleaning element.

9. The cleaning device according to claim 8, wherein the bristles or bristle loops are folded out extending from the cleaning element.

10. The cleaning device according to claim 8, wherein the strip forming the cleaning element has an extended portion on one end.

11. The cleaning device according to claim 1, wherein the handle shaft is hollow.

12. A method for cleaning or debridement of surfaces and holes in teeth of a subject using a cleaning device, wherein the method comprises:
   attaching a cleaning device to a rotation device, wherein the cleaning device comprises two combined main parts,
      the first main part being a handle shaft which is elastically deformable;
      the second main part being a cleaning element comprising a base part and several bristles, bristle loops or a cam of spikes coupled to the base part, wherein the bristles, bristle loops or cam of spikes are made of a metal, metal alloy or a polymeric material, wherein the cleaning element with its base part and several bristles, bristle loops or a cam of spikes is made from one piece, wherein the cleaning element is in the form of a strip which is wound around the handle shaft to be joined together with the same; and wherein
      the base part is joined together with the handle shaft so as to form a cleaning device with a handle; and wherein the cleaning device is adapted so that it can be connected to a rotation device;
   applying the cleaning device to one or more teeth of the subject;
   operating the rotation device to rotate the cleaning device for cleaning or debridement of surfaces and holes in the teeth.

13. A method for cleaning or debridement of an implant surface using a cleaning device, wherein the method comprises:
   attaching the cleaning device to a rotation device, wherein the cleaning device comprises two combined main parts,
      the first main part being a handle shaft which is elastically deformable;
      the second main part being a cleaning element comprising a base part and several bristles, bristle loops or a cam of spikes coupled to the base part, wherein the bristles, bristle loops or cam of spikes are made of a metal, metal alloy or a polymeric material, wherein the cleaning element with its base part and several bristles, bristle loops or a cam of spikes is made from one piece, wherein the cleaning element is in the form of a strip which is wound around the handle shaft to be joined together with the same; and wherein
      the base part is joined together with the handle shaft so as to form a cleaning device with a handle; and wherein the cleaning device is adapted so that it can be connected to a rotation device;
   applying the cleaning device to the implant;
   operating the rotation device to rotate the cleaning device for cleaning or debridement of the implant.

\* \* \* \* \*